United States Patent [19]  
Ikeda et al.

[11] Patent Number: 4,902,810  
[45] Date of Patent: Feb. 20, 1990

[54] PROCESS FOR THE PRODUCTION OF HEXAFLUOROPROPYLENE OXIDE

[75] Inventors: Masanori Ikeda; Morikazu Miura, both of Shizuoka; Atsushi Aoshima, Kanagawa, all of Japan

[73] Assignee: Asahi Kogaku Kogyo Kabushiki Kaisha, Tokyo, Japan

[21] Appl. No.: 72,189

[22] Filed: Jul. 6, 1987

Related U.S. Application Data

[63] Continuation of Ser. No. 375,632, May 6, 1982, abandoned.

[30] Foreign Application Priority Data

May 6, 1981 [JP] Japan .................... 56-67834  
Dec. 19, 1981 [JP] Japan .................... 56-205581  
Dec. 26, 1981 [JP] Japan .................... 56-210487  
Feb. 4, 1982 [JP] Japan .................... 57-15539

[51] Int. Cl.$^4$ ........................... C07D 301/24  
[52] U.S. Cl. ........................... 549/521; 549/520  
[58] Field of Search ................ 549/521, 520

[56] References Cited

U.S. PATENT DOCUMENTS

| | | | |
|---|---|---|---|
| 2,700,686 | 1/1955 | Dickey et al. | 549/521 |
| 3,313,829 | 4/1967 | Rosenblatt et al. | 549/520 |
| 3,358,003 | 12/1967 | Eleuterio | 549/531 |
| 3,536,733 | 10/1970 | Carlson | 549/523 |
| 3,996,259 | 12/1976 | Lee et al. | 549/520 |
| 4,006,169 | 2/1977 | Anderson et al. | 549/520 |
| 4,098,831 | 7/1978 | Marsh | 260/646 |
| 4,356,291 | 10/1982 | Darling | 525/403 |

FOREIGN PATENT DOCUMENTS 176314 6/1981 Hungary .

OTHER PUBLICATIONS

T. H. Lowry et al., *Mechanism and Theory in Organic Chemistry*, Harper & Row, p. 62, (1976).  
F. Ishi et al., *Synthesis*, 1980, 706.  
Chemical Abstracts, 95, 80184n, (1981).  
S. Krishnan, *J. Am. Chem. Soc.*, 99, 8121, (1977).  
Weber et al., *Phase Transfer Catalysts in Organic Synthesis*, (Japanese Version), pp. 25 and 119 to 120.  
C. M. Starks, *Phase Transfer Catalysts*, Academic Press, pp. 112 to 125, 140 to 154, (1979).  
W. P. Weber et al., *Jour. Chem. Education*, vol. 55, (1978), pp. 429 to 433.  
C. M. Starks, *Phase Transfer Catalysts*, Academic Press, pp. 170 and 306.  
D. C. England et al., *J. Flourine Chem.*, 3, 63, (1973).  
W. Dmowski et al., *J. Fluorine Chem.*, 9, 94, (1977).  
R. D. Dresdner et al., *J. Org. Chem.*, 30, 3524, (1965).  
Millauer et al., *Angew. Chem. Int. Ed. Engl.*, 24, 161 to 179, (1985).  
D. Sianesi et al., *J. Org. Chem.*, 31, 2312, (1966).  
Chemical Abstracts, 89, 23715p, (1978).  
G. H. Coleman, *J. Amer. Chem. Soc.*, 55, 3001, (1933).  
C. Bachand et al., *J. Org. Chem.*, 39, 3136, (1974).  
Iordache et al., *Rev. Chem.*, (Bucharest), (1979), 30 (7), 629 to 632, (Translated portion).  
Chemical Abstracts, 92, 58181a, (1980).  
I. P. Kolenko et al., *Izu. Akad. Nauk SSSR Ser. Khim.*, (1979), "Fluoroolefin Oxides," No. 11, pp. 2509–2512.

(List continued on next page.)

Primary Examiner—Richard L. Raymond  
Attorney, Agent, or Firm—Sughrue, Mion, Zinn, Macpeak & Seas

[57] ABSTRACT

A process for producing hexafluoropropylene oxide from hexafluoropropylene is described. The process comprises epoxidizing hexafluoropropylene in a two-phase system of an aqueous phase and an organic phase by the use of a hypochlorite as an oxidizing agent, the hypochlorite being dissolved or dispersed in the aqueous phase, in the presence of at least one catalyst selected from the group consisting of (a) quaternary ammonium salts, (b) quaternary phosphonium salts, (c) quaternary arsonium salts, and (d) lipophilic complexing agents for cations contained in the hypochlorite, and also, in the presence or absence of an inorganic base.

14 Claims, 1 Drawing Sheet

OTHER PUBLICATIONS

J. M. McIntosh, *J. Chem. Ed.,* (1978), "Phase-Transfer Catalysts Using Quaternary Ominum Salts," 55, pp. 235–238.

G. W. Gokel et al., *J. Chem. Ed.,* (1978), "Phase Transfer Catalyst," 55, pp. 350–354.

Kelly et al., *Polymer,* (1979), "Linear Polymers and Block Copolymers as Solid–Liquid Phase Transfer Catalysts," 20, pp. 1048–1050.

*Chemical Abstracts,* 95:60668v, "Introduction by Experiments to Phase Transfer Catalysts," Koch, H., (1981).

*Chemical Abstracts,* 92:65502j, "Polyethylene Glycol Derivatives as Complexing Agents and Phase Transfer Catalysts," Toke, L., (1980).

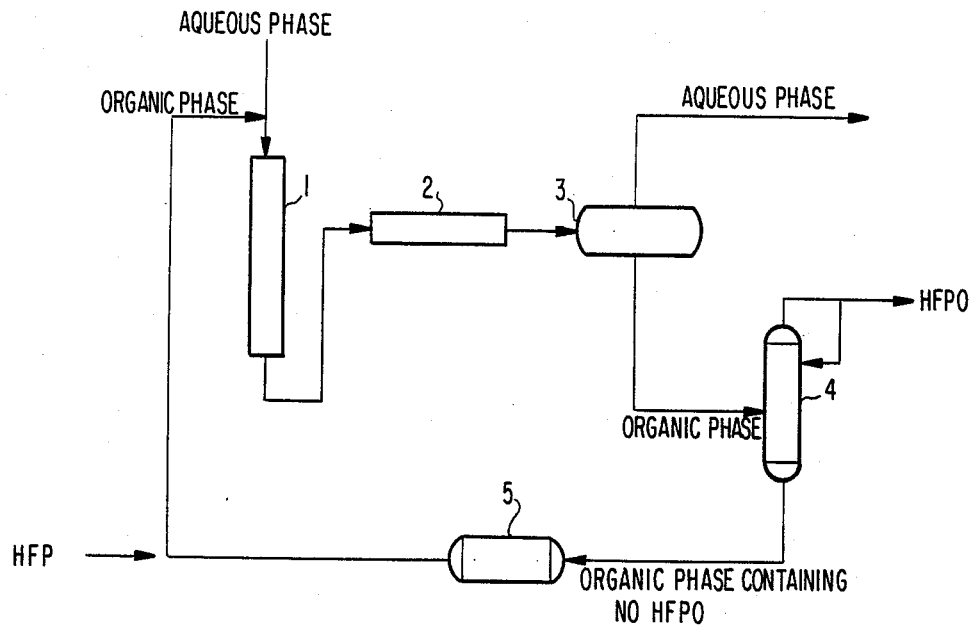

PROCESS FOR THE PRODUCTION OF HEXAFLUOROPROPYLENE OXIDE

This application is a continuation of application Ser. No. 06/375,632 filed May 6, 1982, now abandoned.

FIELD OF THE INVENTION

The present invention relates to a process for the production of hexafluoropropylene oxide, and more particularly, to a process for producing hexafluoropropylene oxide (hereinafter sometimes referred to as "HFPO") from hexafluoropropylene hypochlorite as an oxidizing agent.

BACKGROUND OF THE INVENTION

Hexafluoropropylene oxide is an intermediate which is used to prepare useful fluorine-containing compounds such as hexafluoroacetone and perfluorovinyl ether, as described in U.S. Pat. No. 4,165,340. Furthermore, polymers of HFPO have a wide variety of uses, e.g., a heat transfer medium and lubricant oil, as described in U.S. Pat. Nos. 3,660,315 and 3,775,439.

Hexafluoropropylene oxide can be prepared by epoxidization of hexafluoropropylene. It is, however, difficult to epoxidize hexafluoropropylene by the same method used in the epoxidization of propylene or allyl chloride since hexafluoropropylene has chemical properties which are very different from those of hydrocarbon olefins such as propylene or chlorinated hydrocarbon olefins such as allyl chloride.

For example, both propylene and allyl chloride can be epoxidized by the chlorohydrin process. In the process propylene or allyl chloride is first converted into chlorohydrin and, thereafter, ring closure is achieved by the use of alkalis. On the other hand, when the chlorohydrin process is used to epoxidize hexafluoropropylene, decomposition of the resulting chlorohydrin into carbonyl compounds occurs because of its instability, and it is therefore impossible to prepare the desired hexafluoropropylene oxide from the chlorohydrin.

Various methods for epoxidization of hexafluoropropylene have heretofore been proposed, which are different from those for hydrocarbon olefins and chlorinated hydrocarbon olefins. However, none of these methods can be used advantageously for the production of hexafluoropropylene oxide on a commercial scale.

Typical known methods of production of hexafluoropropylene oxide include the method described in U.S. Pat. 3,358,003 wherein hexafluoropropylene is oxidized into hexafluoropropylene oxide in a medium of alkaline hydrogen peroxide and the method described in U.S. Pat. No. 3,536,733 wherein hexafluoropropylene is oxidized into hexafluoropropylene oxide in the presence of an inert solvent. In accordance with these methods, however, it is not possible to obtain hexafluoropropylene oxide in good yields since the reaction is difficult to control, decomposition of hexafluoropropylene oxide formed is difficult to prevent, or large amounts of by-products are formed. Furthermore, when the HFP conversion is increased, the HFPO selectivity is lowered. Therefore, in order to efficiently use hexafluoropropylene, it is necessary to stop the reaction at low HFP conversions and to separate and recover unreacted hexafluoropropylene from hexafluoropropylene oxide for reuse. However, since the boiling point of hexafluoropropylene ($-29.4°$ C.) is very near that of hexafluoropropylene oxide ($-27.4°$ C.), it is difficult to separate them by distillation. Therefore, it is necessary to employ a specific separation technique. For this purpose, there has been proposed a method in which hexafluoropropylene is reacted with bromine in order to convert it into a high-boiling dibromo compound. This compound is then separated from hexafluoropropylene oxide as the dibromo compound. Another proposed method is an extractive distillation separation method as described in U.S. Pat. No. 3,326,780 and 4,134,796. These methods, however, are complicated and seriously increase the production cost of hexafluoropropylene oxide.

It is known, as described in IZV. AKAD. NAUK. SSSR. SER. KHIM., 79, (11) 2509, that hexafluoropropylene oxide is formed from hexafluoropropylene in a system comprising an aqueous hypochlorite solution with a polar solvent, e.g., acetonitrile and diglyme added thereto. Investigations of the oxidation method using such hypochlorites have revealed that the HFPO selectivity is about 10%. Thus it has been found that it is not possible to prepare hexafluoropropylene oxide in good yields. The reason for this is believed to be that since the reaction system is a homogeneous mixture of the polar solvent and the aqueous hypochlorite solution, the hexafluoropropylene oxide formed readily reacts with water under alkaline conditions, resulting in the decomposition thereof. Furthermore, this method requires an additional step to recover the polar solvent from the reaction system after the reaction. In view of the above described defects, the method is not suitable for practical use in the production of hexafluoropropylene oxide.

SUMMARY OF THE INVENTION

As a result of extensive investigations to develop a method of producing hexafluoropropylene oxide from hexafluoropropylene by a simplified procedure and in high yields, it has been found that hexafluoropropylene oxide can be prepared from hexafluoropropylene in high yields in a two-phase system. The two phases are an aqueous phase and an organic phase wherein a hypochlorite is used as an oxidizing agent. The agent is dissolved or dispersed in the aqueous phase, and at least one compound selected from the group consisting of (a) quaternary ammonium salts, (b) quaternary phosphonium salts, (c) quaternary arsonium salts, and (d) lipophilic complexing agents for cations contained in hypochlorites is used as a catalyst.

The present invention, therefore, provides a process for producing hexafluoropropylene oxide from hexafluoropropylene which comprises epoxidizing hexafluoropropylene in a two-phase system of an aqueous phase and an organic phase using a hypochlorite as an oxidizing agent, said hypochlorite being dissolved or dispersed in the aqueous phase, in the presence of at least one catalyst selected from the group consisting of (a) quaternary ammonium salts, (b) quaternary phosphonium salts, (c) quaternary arsonium salts, and (d) lipophilic complexing agents for cations contained in the hypochlorite, and in the presence or absence of an inorganic base.

BRIEF DESCRIPTION OF THE DRAWINGS

The FIGURE is one example of flow diagram illustrating a process for continuous production of hexafluoropropylene oxide from hexafluoropropylene according to the invention.

DETAILED DESCRIPTION OF THE INVENTION

In the two-phase reaction of the invention, almost all of hexafluoropropylene and formed hexafluoropropylene oxide are present in the organic phase. The process of the invention offers the advantage that hexafluoropropylene oxide can be obtained at high selectivity even if the HFP conversion is increased. The reason for this is believed to be that since the formed hexafluoropropylene oxide is present in a phase different from the alkaline aqueous solution, the decomposition of hexafluoropropylene oxide resulting from contact with the alkaline aqueous solution is prevented from occurring. In accordance with the process of the invention, therefore, it is possible to omit a tedious step of separating hexafluoropropylene oxide from hexafluoropropylene and a step of recycling hexafluoropropylene by increasing the HFP conversion.

After the reaction, the organic phase and the aqueous phase are separated, and from the organic phase, hexafluoropropylene oxide can be easily isolated by separation techniques, e.g., distillation. Since the residual organic phase from which hexafluoropropylene oxide has been removed contains the catalyst and, therefore, can be recycled and reused as such, recovery of the solvent or catalyst is greatly simplified.

Thus, in the process of the invention, hexafluoropropylene oxide can be produced in high yields and the process of production is greatly simplified. This will reduce the initial cost or construction cost of the reaction equipment and the operation cost. Therefore, the present invention is an economical production of hexafluoropropylene oxide.

The invention will hereinafter be explained in greater detail.

Hypochlorites which can be used in the invention include alkali metal salts, e.g., lithium hypochlorite, sodium hypochlorite, potassium hypochlorite, rubidium hypochlorite, and cesium hypochlorite, and alkaline earth metal (excluding beryllium) salts, e.g., magnesium hypochlorite, calcium hypochlorite, strontium hypochlorite, and barium hypochlorite. Of these compounds, sodium hypochlorite and calcium hypochlorite are particularly suitable for use in the invention because they are produced on a commercial scale for bleaching agents, sterilizers, etc., and are available inexpensively. Commercially available hypochlorites may be used as such, or hypochlorites prepared from inorganic bases and chlorine gas or hypochlorites prepared by electrolysis of inorganic chlorides in undivided cell may be used.

The hypochlorite as used herein is dissolved mainly in the aqueous phase, and the concentration of the hypochlorite in the aqueous phase is not subject to any special limitations. In general a preferred available chlorine content is within the range of from 1% to 25%, with the range of from 3% to 20% being particularly preferred. When the available chlorine content is too low, it is necessary to process a large amount of aqueous phase, which is disadvantageous from an economic standpoint. On the other hand, when the available chlorine content is too high, the hypochlorite becomes instable, causing handling difficulties.

The ratio of hypochlorite to hexafluoropropylene is not critical and can be determined optionally. Usually satisfactory results are obtained when the hypochlorite is added in an amount, as calculated as hypochlorite ion, of from 0.5 to 30 gram equivalent per mole of the hexafluoropropylene, with the range of from 0.8 to 10 gram equivalent being preferred and the range of from 1 to 5 gram equivalent being particularly preferred.

The process of the invention can be carried out either in the presence of inorganic bases or in the absence of inorganic bases. The practice of the reaction in the presence of inorganic bases offers the following advantages. One of the advantages is that the HFPO selectivity can be held at high levels even if the HFP conversion is increased. Therefore, without any serious reduction in the HFPO selectivity, the HFP conversion can be increased in order to decrease the amount of the residual HFP. This permits production of hexafluoropropylene oxide of high purity in high yields without a step of separating hexafluoropropylene oxide from hexafluoropropylene. Another advantages is that good results can be obtained even if the ratio of the hypochlorite to the hexafluoropropylene is lowered. When the reaction is carried out in the absence of the inorganic base or in the presence of a very small amount of inorganic base, if the ratio of the hypochlorite to the hexafluoropropylene is lowered, the HFPO selectivity is reduced, and the residual available chlorine content is reduced in the course of the reaction. This leads to no further increase in the HFP conversion. In this case, therefore, it is necessary to carry out the reaction in the presence of an excessive amount of hypochlorite in order to obtain good results. On the other hand, if the process of the invention is performed in the presence of a specific amount of inorganic base, the amount of the hypochlorite being used can be reduced. This permits reduction in the production cost associated with the reduction in the amount of the hypochlorite being used, reduction in the size of the reaction equipment and reduction in the cost of disposal processing.

Inorganic bases which can be used in the process of the invention include alkali metal hydroxides, e.g., lithium hydroxide, sodium hydroxide, potassium hydroxide, rubisium hydroxide, and cesium hydroxide, and alkaline earth metal hydroxides, e.g., calcium hydroxide, strontium hydroxide, and barium hydroxide. These inorganic bases may be completely dissolved in the aqueous phase, or may not be completely dissolved and be partially present as a solid phase. Of the above described inorganic bases, sodium hydroxide is particularly suitable for use in the invention in view of cost, solubility in water, ease of handling, and so forth.

The amount of the inorganic base used in the process of the invention is not critical and can be determined appropriately. In order to yield the above described advantages, the inorganic base is added in an amount of at least 0.1 gram equivalent per mole of hexafluoropropylene. The total amount of the inorganic base may be introduced into the reaction system from the beginning of the reaction, or in some cases, it may be added in appropriate portions in the course of the reaction.

At least one compound selected from the group consisting of (a) quaternary ammonium salts, (b) quaternary phosphonium salts, (c) quaternary arsonium salts, and (d) lipophilic complexing agents for cations contained in hypochlorites is used as a catalyst in the process of the invention. Preferably, the catalyst has an affinity with the organic phase.

Quaternary ammonium salts which can be used in the invention include those represented by the general formula (I):

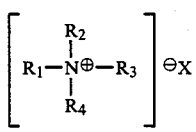 (I)

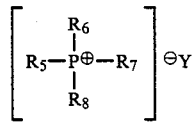 (II)

wherein $R_1$, $R_2$, $R_3$ and $R_4$ may be either the same or different, and each represents a hydrocarbon group which is unsubstituted or substituted by a functional group which is inert under the reaction conditions. The type and length of the hydrocarbon group are selected appropriately depending on the type of the solvent used, the rate of reaction required, and so forth. Examples of such hydrocarbon groups include an alkyl group, an alkenyl group, a cycloalkyl group, a cycloalkenyl group, an aryl group, an aralkyl group, and an alkenylaryl group. Of these groups, an alkyl group, an aryl group, and an aralkyl group are particularly preferred. With regard to the length of the hydrocarbon group, the total number of carbon atoms contained in $R_1$, $R_2$, $R_3$ and $R_4$ is usually from 6 to 100, preferably from 8 to 70, and particularly preferably from 10 to 50, per quaternary ammonium ion. Inert functional groups which can be used as substituents for the hydrocarbon group are limited depending on the reaction conditions. Usually a halogen atom, an acyl group, a carboxy group, an ester group, a nitrile group, an alkoxyl group, etc. are used. Rhd 1 and $R_2$, or $R_1$, $R_2$ and $R_3$ may combine together to form a nitrogen-containing heterocyclic ring, or $R_1$, $R_2$, $R_3$ or $R_4$ may constitute a part of a polymeric compound.

Quaternary ammonium ions which can be used include a tetraethylammonium ion, a tetra-n-propylammonium ion, a tetra-n-butylammonium ion, a tri-n-octylmethylammonium ion, a cetyltrimethylammonium ion, a benzyltrimethylammonium ion, a benzyltriethylammonium ion, a cetylbenzyldimethylammonium ion, a cetylpyridinium ion, a n-dodecylpyridinium ion, a phenyltrimethylammonium ion, a phenyltriethylammonium ion, a N-benzylpicolinium ion, a pentamethonium ion, and a hexamethonium ion. Of these, quaternary ammonium ions having a long-chain alkyl group such as a tri-n-octylmethylammonium ion and a tetra-n-butylammonium ion are preferably used.

Anions, $\ominus X$, in the general formula (I) are not subject to any special limitation, and various kinds of anions can be used. Usually, halogen ions, mineral acid ions excluding the halogen ions, organic acid ions, hydroxyl ion and so forth are used.

Examples of such anions include a chloride ion, a bromide ion, an iodide ion, a fluoride ion, a hydrogensulfate ion, a sulfate ion, a nitrate ion, a phosphate ion, a perchlorate ion, a hydroxide ion, an acetate ion, a benzoate ion, a benzenesulfonate ion, and a p-toluenesulfonate ion. Of these ions, a chloride ion, a hydrogensulfate ion, and a hydroxide ion are particularly preferred.

Quaternary phosphonium salts which can be used in the invention include those represented by the general formula (II):

wherein $R_5$, $R_6$, $R_7$ and $R_8$ may be the same or different, and each represents a hydrocarbon group which is unsubstituted or substituted by a functional group which is inert under the reaction conditions. The type and length of the hydrocarbon group are determined appropriately depending on the type of the solvent used, the rate of reaction required, and so forth. Examples of such hydrocarbon groups include an alkyl group, an alkenyl group, a cycloalkyl group, a cycloalkenyl group, an aryl group, an aralkyl group, and an alkenylaryl group. Of these groups an alkyl group, an aryl group, and an aralkyl group are particularly preferred. With regard to the length of the hydrocarbon group, the total number of carbon atoms contained in $R_5$, $R_6$, $R_7$ and $R_8$ is usually from 6 to 100, preferably from 8 to 70, and particularly preferably from 10 to 50, per quaternary phosphonium ion. Inert functional groups which can be used as substituents for the hydrocarbon group are limited by the reaction conditions. Usually, a halogen atom, an acyl group, a carboxyl group, an ester group, a nitrile group, and an alkoxyl group are used. $R_5$ and $R_6$, or $R_5$, $R_6$ and $R_7$ may combine together to form a heterocyclic ring, or $R_5$, $R_6$, $R_7$ and $R_8$ may form a part of the polymeric compound.

Examples of quaternary phosphonium ions include a tetraethylphosphonium ion, a tetra-n-butylphosphonium ion, a tri-n-octylethylphosphonium ion, a cetyltriethylphosphonium ion, a cetyltri-n-butylphosphonium ion, a n-butyltriphenylphosphonium ion, a n-amyltriphenylphosphonium ion, a n-hexyltriphenylphosphonium ion, a n-heptyltriphenylphosphonium ion, a methyltriphenylphosphonium ion, a benzyltriphenylphosphonium ion, and a tetraphenylphosphonium ion. Of these, quaternary phosphonium ions having a long-chain alkyl group such as a tri-n-octylethylphosphonium ion and a tetra-n-butylphosphonium ion are perferably used.

Anions, $\ominus Y$, in the general formula (II) are not subject to any special limitations, and various kinds of anions can be used. Usually, halogen ions, mineral acid ions excluding the halogen ions, organic acid ions, and so forth are used.

Examples of such anions include a chloride ion, a bromide ion, an iodide ion, a fluoride ion, a hydrogensulfate ion, a sulfate ion, a nitrate ion, a phosphate ion, a perchlorate ion, and a p-toluenesulfonate ion. Particularly preferred are a chloride ion and a bromide ion.

Quaternary arsonium salts as used herein are sufficient to have an affinity to the organic phase and to be capable of providing quaternary arsonium ions which are stably present under the reaction conditions of the invention. Examples include tetraarylarsonium salts such as tetraphenylarsonium chloride and tetraphenylarsonium bromide, triarylalkylarsonium salts such as triphenylmethylarsonium chloride, and their polymeric derivatives.

Lipophilic complexing agents for cations contained in hypochlorites are required to have both an ability with respect to complexing the cations and an affinity to the organic phase, and naturally, to be stable under the reaction conditions of the invention. Any complexing agents meeting the above requirements can be used in the invention, and thus a wide variety of compounds are useful.

Typical examples of the lipophilic complexing agents which can be used in the invention are shown below although the invention is not limited thereto.

(1) Large Ring Compounds

Large ring compounds are commonly called "crown ethers" (as described in, for example, Pedersen, *J. Amer. Chem. Soc.*, 89, 2495, 7017 (1967)), and are known to have a high coordination ability to alkali metal ions and alkaline earth metal ions. Almost all of such crown ethers are represented by the general formula (III), including their substituted derivatives.

(III)

wherein n is an integer of from 4 to 20, m is an integer of from 1 to n, and $l_1$, $l_2$, --- and $l_n$ which may be the same or different, each is an integer of from 2 to 4.

Examples of such crown ethers (named according to the Pedersen's nomenclature) include 18-crown-6, dicyclohexyl-18-crown-6, dibenzo-18-crown-6, benzo-15-crown-5, dibenzo-15-crown-5, dibenzo-21-crown-7, dibenzo-24-crown-8-, dibenzo-30-crown-10, and dicyclohexyl-24-crown-8.

(2) Large Ring Aminoethers

Examples of large ring aminoethers are bicyclic aminoethers and monocyclic aminoethers.

Bicyclic aminoethers are commonly called "cryptands" (as described in, for example, Lehn, Tetrahedron Lett., 2885, 2889 (1969)), and are known to have a very high coordination ability to alkali metal ions and alkaline earth metal ions. Almost all of cryptands are represented by the general formula (IV), including their substituted derivatives.

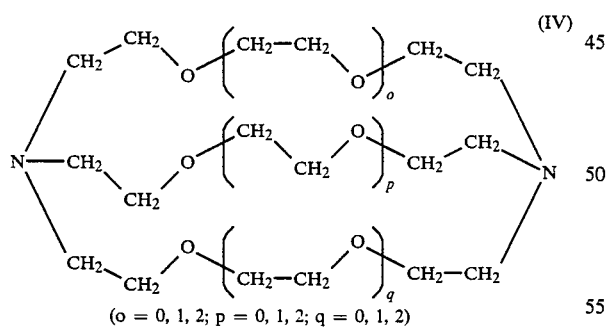
(IV)

(o = 0, 1, 2; p = 0, 1, 2; q = 0, 1, 2)

Preferred examples of such cryptands are shown below:

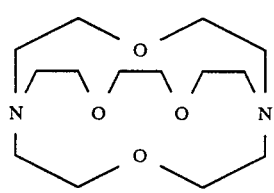
(IV-a)

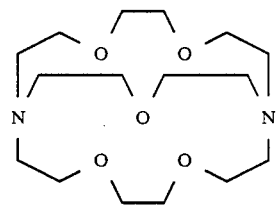
(IV-b)

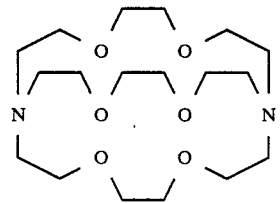
(IV-c)

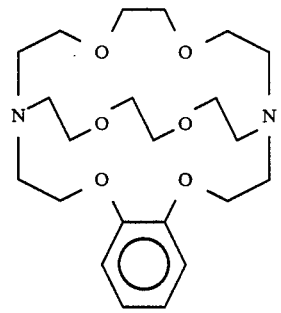
(IV-d)

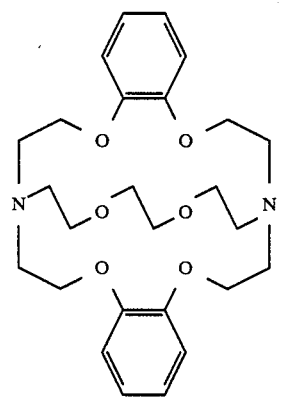
(IV-e)

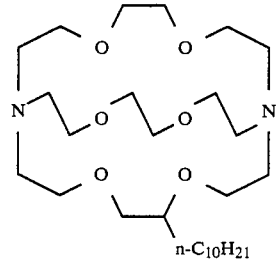
(IV-f)

-continued (IV-g)
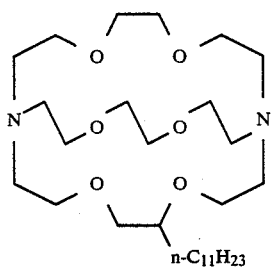

(IV-h)
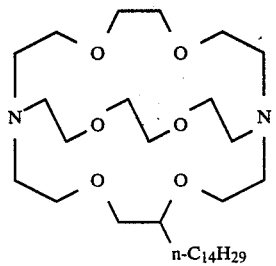

Examples of monocyclic aminoethers include those compounds represented by the general formula (V) and their substituted derivatives.

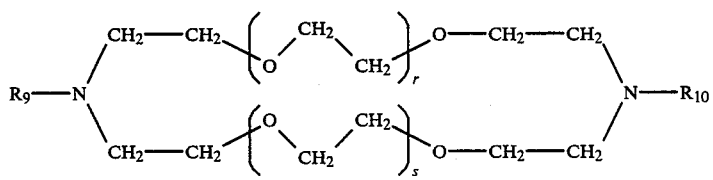
(V)

wherein r=0, 1 or 2; s=0, 1 or 2; and $R_9$ and $R_{10}$, each represents H or a substituted or unsubstituted hydrocarbon group containing from 1 to 80 carbon atoms.
Preferred examples are shown below:

(V-a)
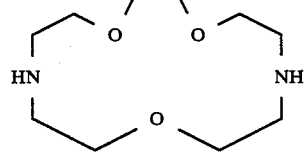

(V-b)
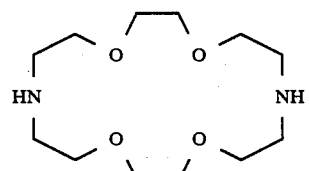

(V-c)
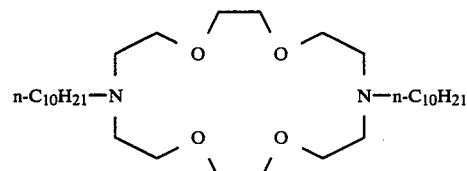

-continued (V-d)
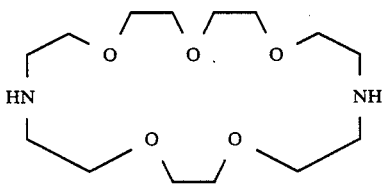

(3) Polyethylene Glycol and Its Derivatives

Various kinds of polyethylene glycols can be used. Those having a degree of polymerization of at least 10 are preferred.

Polyethylene glycol derivatives include the compounds represented by the general formula (VI) or (VII) and their substituted derivatives, copolymers of ethylene oxide and other monomers, and surface active agents containing the polyethylene glycol structure.

$$R_{11}O\text{-}(CH_2\text{---}CH_2\text{---}O)_t\text{H} \quad (VI)$$

(wherein t=5 or more; and $R_{11}$ represents a substituted or unsubstituted hydrocarbon group containing from 1 to 80 carbon atoms)

$$R_{12}O\text{-}(CH_2\text{---}CH_2\text{---}O)_u R_{13} \quad (VII)$$

(wherein u=3 or more; and $R_{12}$ and $R_{13}$, each represents a substituted or unsubstituted hydrocarbon group).

Preferred examples of the polyethylene glycol derivatives represented by the general formula (VI) or (VII) are shown below:

n-$C_{16}H_{33}$O-(CH₂—CH₂—O)₁₂-H     (VI-a)

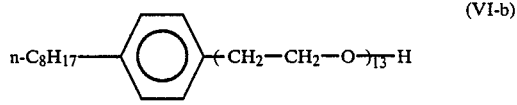
(VI-b)

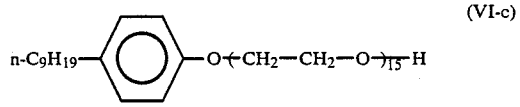
(VI-c)

CH₃O-(CH₂—CH₂—O)₂₅CH₃     (VII-a)

n-C₄H₉O-(CH₂—CH₂—O)₁₀-n-C₄H₉     (VII-b)

-continued

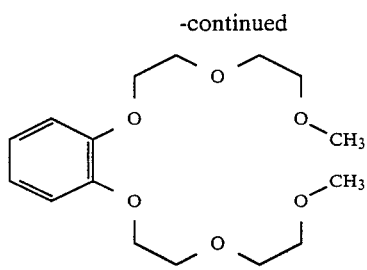 (VII-c)

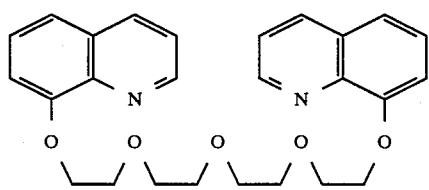 (VII-d)

An example of a copolymer of ethylene oxide and other monomers is an ethylene oxide-propylene oxide block copolymer.

Examples of surface active agents containing the polyethylene glycol structure include polyoxyethylene alkylthio ether, polyoxyethylene alkylamine, polyoxyethylene alkyl ether sulfuric acid ester salts, polyoxyethylene alkyl phenyl ether sulfuric acid ester salts, polyoxyethylene carboxylate, polyoxyethylene-type alkylolamide, and polyoxyethylene alkyl ether.

(4) Polyvinyl Pyrrolidone and Its Derivatives

Polyvinyl pyrrolidone derivatives include copolymers of vinyl pyrrolidone and other monomers.

(5) Amineoxides represented by the general formula (VIII) and their substituted derivatives $$R_{14}R_{15}R_{16}N \rightarrow O \qquad (VIII)$$

wherein $R_{14}$, $R_{15}$ and $R_{16}$, each is a hydrocarbon group, the total number of carbon atoms contained in $R_{14}$, $R_{15}$ and $R_{16}$ is at least 10, and $R_{14}$ and $R_{15}$, $R_{14}$, $R_{15}$ and $R_{16}$ may combine together to form a nitrogen-containing heterocyclic ring.

Examples include tri-n-octylamineoxide and 4-(5-nonyl)pyridine-N-oxide.

(6) Compounds resulting from substitution of one or more or all oxygen atoms in large ring polyethers, large ring aminoethers, polyethylene glycol, polyethylene glycol derivatives, and their substituted derivatives by nitrogen atom

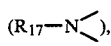, sulfur atom, phosphorus atom

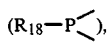, amineoxide group

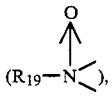, sulfinyl group, sulfonyl group or the group

(wherein $R_{17}$, $R_{18}$ and $R_{19}$, each is a hydrogen atom, or a substituted or unsubstituted hydrocarbon group).

Examples of these compounds are shown below:

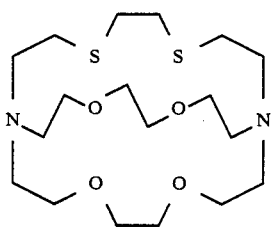 (IX-a)

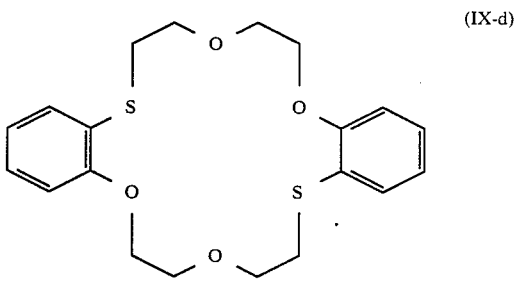 (IX-b)

(IX-c)

(IX-d)

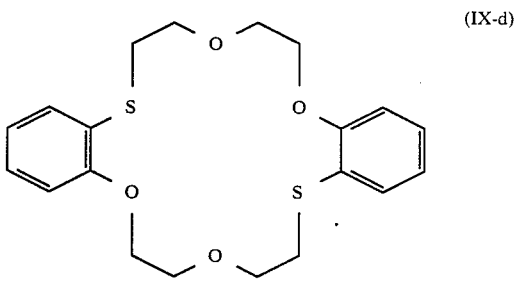

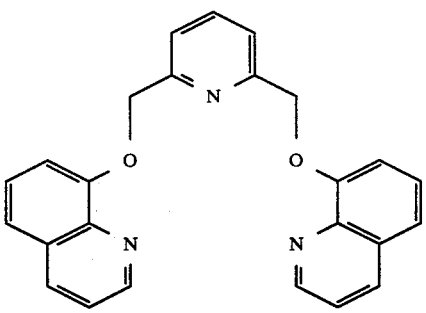

(IX-e)

In addition to the above described lipophilic complexing agents, various compounds containing functional groups, such as a carbonyl group, a sulfinyl group, a sulfonyl group phosphoryl group, an ether group, an amino group, an imidazole ring, a furan ring, and a pyridine ring, having a coordination ability to metal cations can be used in the process of the invention. These lipophilic complexing agents may be supported on polymeric compounds or various insoluble carriers by various supporting techniques.

The amount of the catalyst used in the process of the invention is selected appropriately depending on the structure of the catalyst, the type of the solvent, the reaction temperature, the requisite rate of reaction, and so forth. Usually the catalyst is used in an amount of from 0.0001 to 10 moles per gram equivalent of hypochlorite ion, with the range of from 0.001 to 1 mole being particularly preferred. When the amount of the catalyst is too small, the rate of reaction is unsuitably low, whereas when the catalyst is used in an excess amount, the rate of reaction is so high that it is difficult to control the reaction, and the cost of the catalyst increases, which is disadvantageous from an economic standpoint.

The reaction of the invention is carried out in a two-phase system of an aqueous phase and an organic phase. In this case, the organic phase is sufficient to form a phase which contains hexafluoropropylene and is different from the aqueous phase. It is not necessary for the organic phase to meet any further requirements. For example, the organic phase may be either a phase composed mainly of hexafluoropropylene per se, or a phase composed of a water sparingly soluble catalyst and hexafluoropropylene, or a phase composed of an inert solvent and hexafluoropropylene, said inert solvent being substantially immiscible or sparingly miscible in the aqueous phase.

In the practice of the invention, it is only necessary that there be an organic phase containing substantially all hexafluoropropylene and an aqueous phase containing the hypochlorite. Thus, there may be present one or more different phases in the system in addition to the two phases. For example, either in a system wherein the organic phase consists of two phases composed of different media having low mutual solubilities with each other, or in a system wherein the catalyst is supported on a water-insoluble carrier, forming a third phase, the process of the invention can be carried out.

Organic solvents which are used to form the organic phase are inert solvents which are substantially immiscible or sparingly miscible in the aqueous phase. Examples of such inert solvents include aliphatic hydrocarbons, e.g., n-hexane, n-octane, and n-decane; alicyclic hydrocarbons, e.g., cyclohexane, methylcyclohexane, and decalin; aromatic hydrocarbons, e.g., benzene, toluene, and xylene; ethers, e.g., diisopropyl ether and di-n-butyl ether; chlorinated hydrocarbons, e.g., methylene chloride, chloroform, carbon tetrachloride, 1,2-dichloroethane, and chlorobenzene; chlorofluorocarbons, e.g., 1,2-dichloro-1,1,2,2-tetrafluoroethane, fluorotrichloromethane, 1,1,2-trichloro-1,2,2-trifluoroethane, and 1,1,2,2-tetrachloro1,2-difluoroethane; perfluorocarbons, e.g., perfluorocyclobutane perfluorodimethylcyclobutane, perfluorohexane, perfluorooctane, perfluorodecane, and hexafluorobenzene; and mixtures thereof. The organic solvent is selected appropriately taking into account the solubility in hexafluoropropylene or hexafluoropropylene oxide, the solubility in the catalyst used in the reaction, the separation capability from the aqueous phase, the reaction conditions, e.g., reaction pressure and reaction temperature, and so forth. Of the above described solvents, fluorine-containing solvents such as chlorofluorocarbons, perfluoro compounds, and partially fluorinated hydrocarbons are suitable for use in the process of the invention because of their high solubilities in hexafluoropropylene or hexafluoropropylene oxide, and also, chlorinated hydrocarbons are suitable for use in the process of the invention because they generally have high solubilities in the catalysts.

The volume ratio of the organic phase to the aqueous phase is not critical and can be determined appropriately depending on the reaction method, the reaction conditions, and so forth. Usually the organic phase is from 0.05 to 20 times as much as the aqueous phase, with the range of from 0.2 to 5 times being particularly preferred.

In the practice of the process of the invention, the reaction temperature is determined according to the amount of the catalyst, the composition of the reaction liquid, the requisite rate of reaction, and so forth. The reaction temperature is usually within the range of from −25° C. to 60° C., preferably within the range of from −20° C. to 40° C., and particularly preferably within the range of from −18° C. to 20° C. When the reaction temperature is too low, the reaction does not proceed at practically acceptable rates, and in extreme cases, the aqueous phase freezes and the reaction does not proceed at all. On the other hand, when the reaction temperature is too high, the decomposition of hexafluoropropylene oxide becomes significant, resulting in a reduction in the HFPO selectivity.

With regard to the reaction pressure, as long as the pressure is high enough to keep the organic phase containing hexafluoropropylene or hexafluoropropylene oxide in a liquid phase, it is not necessary to meet any further requisites. However, the reaction pressure varies depending on the type and composition of the organic phase, and it is usually within the range of from 1 to 20 atmospheric pressures.

The process of the invention can be carried out by a number of methods including a batch method, a semi-flow method, and a flow method. In commercial production, it is preferable to use the flow method.

The process of the invention can be carried out continuously and commercially advantageously, for example, by a method in which hexafluoropropylene oxide is first synthesized from hexafluoropropylene by the two-phase reaction method of the invention. Thereafter, the organic phase and the aqueous phase are separated from each other, the hexafluoropropylene oxide is isolated from the organic phase, and hexafluoropropylene is added to the residual organic phase containing the catalyst which is then re-used in the two-phase reaction.

In carrying out the two-phase reaction by the flow method, there can be employed a counterflow process and a parallelflow process in which the organic phase containing hexafluoropropylene and the catalyst, and the aqueous phase containing the hypochlorite and the inorganic base are brought into contact with each other. In the practice of the two-phase reaction, it is necessary to fully mix the two phases in the reactor. For that purpose, conventional techniques using, for example, a stirring blade or a stationary mixing device can be employed. In the case of the counterflow process, the two-phase reaction and the phase-separation can be carried out simultaneously. On the other hand, as the parallelflow reaction, there can be mentioned a tube-type reaction and a vessel-type flow reaction. In the case of the tube-type reaction, it is necessary for the two phases to pass through a tube-type reactor in the state that they are finely dispersed. It is necessary, therefore, to install a two phase-mixer before the tube type reactor, or to design the tube type reactor so that it includes the two phase-mixer. In the parallelflow reaction, since the organic phase and the aqueous phase are withdrawn from the two-phase reactor while they are mixed together, it is necessary to separate the organic phase and the aqueous phase in a decantor. The aqueous phase after the two-phase reaction contains unreacted hypochlorite, chlorides resulting from the reaction of the hypochlorite, the inorganic base, a part of the catalyst, and various by-products. The aqueous phase is disposed as such, or when the aqueous phase contains large amounts of the unreacted hypochlorite and catalyst, it is possible to recover the hypochlorite and catalyst from the aqueous phase for re-use thereof. The organic phase after the two-phase reaction contains hexafluoropropylene oxide formed, unreacted hexafluoropropylene, catalyst, and so forth. From the organic phase, hexafluoropropylene oxide and hexafluoropropylene can be easily separated by separation techniques, e.g., distillation. The organic phase from which hexafluoropropylene oxide and hexafluoropropylene have been removed still contains the catalyst. Therefore, after addition of hexafluoropropylene, the organic phase can be returned to the two-phase reaction zone and re-used therein. In the case of several catalysts, part of the catalyst transfers into the aqueous phase during the two-phase reaction, causing a reduction in the catalyst content of the organic phase. In such cases, it is necessary to appropriately supplement the catalyst to the organic phase.

The following Examples and Comparative Examples are given to illustrate the invention in greater detail although the invention is not limited thereto.

The aqueous sodium hypochlorite solutions used in the examples are shown in Table 1.

TABLE 1

| Aqueous Sodium Hypochlorite Solution | Available Chlorine Content (%) | Sodium Hydroxide Concentration (N) |
|---|---|---|
| A*1 | 12 | 0.15 |
| B-0*2 | 12 | 0.025 |
| B-1*3 | 12 | 0.10 |
| B-2*3 | 12 | 1.53 |
| B-3*3 | 12 | 0.40 |
| B-4*4 | 6 | 0.40 |
| C | 10.2 | 0.95 |
| D | 3.8 | 0.40 |

The aqueous sodium hypochlorite solutions of Table 1 were prepared as follows:
*1 Chlorine gas was blown into an aqueous solution of sodium hydroxide maintained at −10° C. to prepare the solution.
*2 Commercially available solution.
*3 Sodium hydroxide was added to Solution B-0 to prepare the solutions.
*4 Sodium hydroxide and water were added to Solution B-0 to prepare the solution.

EXAMPLE 1

A 50-ml pressure bottole in which a stirrer had been placed was charged with the following ingredients:

| | |
|---|---|
| 1,1,2-Tricloro-1,1,2-trifluoroethane (hereinafter referred to as "F-113") | 18 ml |
| Aqueous sodium hypochlorite solution A | 20 ml |
| Hexafluoropropylene | 1.8 g (12 milimoles) |
| Trioctylmethylammonium chloride (hereinafter referred to as "TOMAC") | 0.16 g (0.4 milimoles) |

These ingredients were cooled down to 0° C, and, thereafter, by rotating the stirrer in the reactor with a magnetic stirrer, they were mixed to start the reaction. During the reaction, the temperature was maintained as 0° C. One hour after the start of the reaction, the rotation of the stirrer was stopped. The reaction solution was allowed to stand to separate into an aqueous phase and a F-113 phase. Quantitative analysis of the hexafluoropropylene and hexafluoropropylene oxide contained in the F-113 phase by gas chromatography showed that the HFP conversion was 96% and the HFPO selectivity was 84%.

COMPARATIVE EXAMPLE 1

The procedure of Example 1 was repeated with the exception that TOMAC (catalyst) was not used.

There was obtained only a trace amount of hexafluoropropylene oxide, and almost all hexafluoropropylene was recovered.

EXAMPLE 2 to 15

The procedure of Example 1 was repeated with the exception that 0.16 g of each of the quaternary ammonium salts shown in Table 2 was used in place of TOMAC as a catalyst.

The results are shown in Table 2 below.

TABLE 2

| Example | Catalyst | Reaction Time (hrs) | HFP Conversion (%) | HFPO Selectivity (%) |
|---|---|---|---|---|
| 2 | (n-Bu)$_4$NCl | 2 | 65 | 71 |
| 3 | (n-Bu)$_4$NBr | 3 | 52 | 68 |
| 4 | (n-Bu)$_4$NI | 4 | 53 | 66 |
| 5 | (n-Bu)$_4$NOH | 2 | 57 | 75 |
| 6 | (n-Bu)$_4$NHSO$_4$ | 1 | 66 | 83 |
| 7 | (n-Bu)$_4$NClO$_4$ | 3 | 23 | 74 |
| 8 | Et$_4$NCl | 3 | 11 | 40 |
| 9 | (n-C$_{12}$H$_{25}$)Me$_3$NCl | 3 | 56 | 57 |
| 10 | (n-C$_{14}$H$_{29}$)Me$_2$(PhCH$_2$)NCl | 3 | 65 | 71 |

TABLE 2-continued

| Example | Catalyst | Reaction Time (hrs) | HFP Conversion (%) | HFPO Selectivity (%) |
|---|---|---|---|---|
| 11 | (PhCH$_2$)Me$_3$NCl | 1 | 75 | 52 |
| 12 | 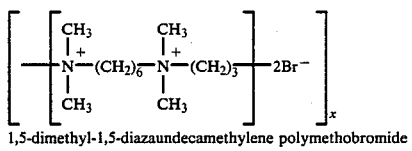 N$^+$—(n-C$_{16}$H$_{33}$)Cl$^-$ | 4 | 33 | 58 |
| 13 | Me—[pyridinium]—N$^+$—CH$_2$PhCl$^-$ | 2 | 22 | 35 |
| 14 | Polybrene ®*[1] | 4 | 33 | 51 |
| 15 | n-C$_{12}$H$_{25}$—N$^+$(CH$_3$)$_2$—CH$_2$—CO$_2^-$ | 2 | 81 | 62 |

*[1]Trade name (Aldrich Chemical Co.)

$$\left[ \begin{array}{cc} \text{CH}_3 & \text{CH}_3 \\ | + & | + \\ -\text{N}-(\text{CH}_2)_6-\text{N}-(\text{CH}_2)_3- \\ | & | \\ \text{CH}_3 & \text{CH}_3 \end{array} \quad 2\text{Br}^- \right]_x$$

1,5-dimethyl-1,5-diazaundecamethylene polymethobromide

EXAMPLES 16 to 22

The procedure of Example 1 was repeated with the exception that 0.60 g (4 milimoles) of hexafluoropropylene was used, and the type of the solvent and the amount of the catalyst, (n-Bu)$_4$NHSO$_4$, were changed as shown in Table 3.

The results are shown in Table 3 below.

TABLE 3

| Example | Solvent | (n-Bu)$_4$NSO$_4$H (g) | Reaction Time (hrs) | HFP Conversion (%) | HFPO Selectivity (%) |
|---|---|---|---|---|---|
| 16 | F-113*[1] | 0.16 | 1.0 | 81 | 77 |
| 17 | PFDMCB*[2] | 0.16 | 3.0 | 87 | 76 |
| 18 | CCl$_4$ | 0.16 | 0.5 | 71 | 76 |
| 19 | CHCl$_3$ | 0.03 | 0.5 | 81 | 56 |
| 20 | CH$_2$Cl$_2$ | 0.03 | 0.5 | 90 | 40 |
| 21 | ClCH$_2$CH$_2$Cl | 0.03 | 0.5 | 93 | 39 |
| 22 | n-hexane | 0.16 | 1.0 | 77 | 74 |

*[1]1,1,2-trichloro-1,2,2-trifluoroethane
*[2]perfluorodimethylcyclobutane

EXAMPLE 23

The procedure of Example 1 was repeated wherein 20 ml of an aqueous solution containing 4.6 g of bleaching powder (composed mainly of calcium hypochlorite) with an available chlorine content of 65% was used in place of 20 ml of the aqueous sodium hypochlorite solution A with an available chlorine content of 12%, 1.5 g of hexafluoropropylene and 0.12 g of TOMAC were used, and the reaction was carried out at a temperature of 20° C. for a period of 15 minutes.

The HFP conversion was 98%, and the HFPO selectivity was 39%.

EXAMPLE 24

The procedure of Example 1 was repeated wherein 30 ml of an aqueous potassium hypochlorite solution with an available chlorine content of 7% was used in place of 20 ml of the aqueous sodium hypochlorite solution A with an available chlorine content of 12%, and 1.5 g of hexafluoropropylene and 0.12 g of TOMAC were used.

The HFP conversion was 41%, and the HFPO selectivity was 53%.

EXAMPLE 25

The procedure of Example 1 was repeated wherein 0.12 g (0.35 milimole) of tetra-n-butylphosphonium bromide was used as a catalyst.

Thirty minutes after the start of the reaction, the HFP conversion was 84%, and the HFPO selectivity was 67%.

EXAMPLE 26

The procedure of Example 25 was repeated wherein the amount of the catalyst, tetra-n-butylphosphonium bromide, was changed from 0.12 g to 0.04 g, and the reaction was carried out at a temperature of 20° C.

The HFP conversion was 71%, and the HFPO selectivity was 62%.

EXAMPLE 27

The procedure of Example 26 was repeated wherein the reaction was carried out at a temperature of 40° C.

The HFP conversion was 83%, and the HFPO selectivity was 54%.

EXAMPLE 28

The procedure of Example 1 was repeated wherein 0.20 g of tetra-n-butylphosphonium bromide was used as a catalyst, and the reaction was carried out at a temperature of −10° C.

The HFP conversion was 77%, and the HFPO selectivity was 69%.

EXAMPLE 29

The procedure of Example 1 was repeated wherein 0.12 g (0.29 milimole) of amyltriphenylphosphonium bromide was used as a catalyst, and the reaction was carried out for a period of 4 hours.

The HFP conversion was 70%, and the HFPO selectivity was 66%.

EXAMPLE 30

The procedure of Example 1 was repeated wherein chloroform was used in place of F-113, 0.04 g (0.12 milimole) of tetra-n-butylphosphonium bromide was used as a catalyst, and hexafluoropropylene was used in the amount of 0.6 g (4 milimoles).

The HFP conversion was 89%, and the HFPO selectivity was 61%.

EXAMPLE 31

The procedure of Example 30 was repeated wherein 0.02 g (0.04 milimole) of hydrochloric acid tetraphenylarsonium chloride ($Ph_4ArCl \cdot HCl$) was used as a catalyst.

The HFP conversion was 78%, and the HFPO selectivity was 74%.

EXAMPLES 32 to 38

The procedure of Example 1 was repeated wherein chloroform was used in place of F-113, hexafluoropropylene was used in the amount of 0.5 g, and as a catalyst, each of the large ring polyethers and large ring aminoethers shown in Table 4 was used.

The results are shown in Table 4 below.

TABLE 4

| Example | Catalyst | Amount of Catalyst (g) | Reaction Time (hrs) | HFP Conversion (%) | HFPO Selectivity (%) |
|---|---|---|---|---|---|
| 32 | 18-crown-6*[1] | 0.36 | 0.5 | 74 | 82 |
| 33 | dibenzo-18-crown*[2] | 0.36 | 2.0 | 84 | 80 |
| 34 | benzo-15-crown-5*[3] | 0.36 | 2.0 | 78 | 81 |
| 35 | cryptofix-222B*[4] | 0.04*[8] | 1.0 | 85 | 74 |
| 36 | cryptofix-221*[5] | 0.12 | 0.5 | 92 | 63 |
| 37 | cryptofix-22*[6] | 0.12 | 2.0 | 86 | 80 |
| 38 | cryptofix-22DD*[7] | 0.12 | 1.0 | 79 | 85 |

The chemical structures of the compounds used are shown below:

*[1]
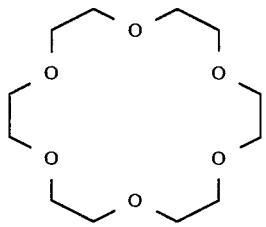

*[2]
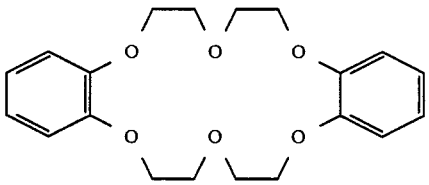

*[3]
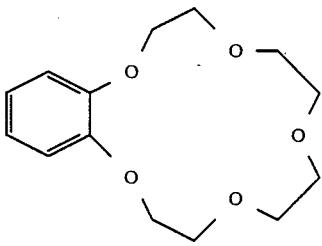

*[4]
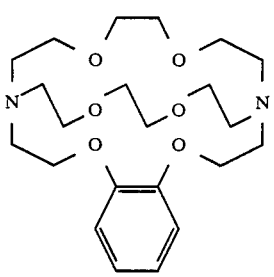

TABLE 4-continued

| Example | Catalyst | Amount of Catalyst (g) | Reaction Time (hrs) | HFP Conversion (%) | HFPO Selectivity (%) |
|---|---|---|---|---|---|
| *5 | (structure below) | | | | |
| *6 | (structure below) | | | | |
| *7 | (structure below) | | | | |

*5

[structure: bicyclic crown ether with two M atoms and six O atoms]

*6

[structure: diaza-crown ether with two HN groups and four O atoms]

*7

[structure: diaza-crown ether with two N-C₁₀H₂₁ groups and four O atoms]

*¹ to *³Named according to the Pederson's nomenculature (J. Am. Chem. Soc., 89, 7071 (1967)).
*⁴ to *⁷Trade names (produced by Merck & Co.)
*⁸50% Toluene solution

EXAMPLE 39

The procedure of Example 1 was repeated wherein 0.24 g of Cryptofix 222B (trade name, produced by Merck & Co.) was used as a catalyst.

Four hours after the start of the reaction, the HFP conversion was 53%, and the HFPO selectivity was 74%.

EXAMPLE 40

The procedure of Example 1 was repeated wherein 0.36 g of a polyether having the formula shown below was used as a catalyst.

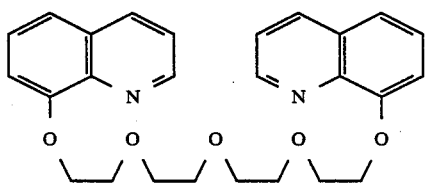

Four hours after the start of the reaction, the HFP conversion was 61%, and the HFPO selectivity was 74%.

EXAMPLE 41

The procedure of Example 1 was repeated wherein 0.12 g of a nonionic surface active agent, polyoxyethylene oleyl ether (produced by Nippon Oils & Fats Co., Ltd.: H.L.B., 16.6), was used as a catalyst.

Three hours after the start of the reaction, the HFP conversion was 75%, and the HFPO selectivity was 76%.

EXAMPLE 42

The procedure of Example 1 was repeated wherein 0.12 g of tri-n-octylamine-N-oxide was used as a catalyst.

Two hours after the start of the reaction, the HFP conversion was 26%, and the HFPO selectivity was 45%.

EXAMPLE 43

The procedure of Example 1 was repeated wherein 0.12 g of 4-(5-nonyl)pyridine-N-oxide was used as a catalyst.

Three hours after the start of the reaction, the HFP conversion was 51%, and the HFPO selectivity was 36%.

EXAMPLE 44

The procedure of Example 32 was repeated wherein 0.36 g of polyvinyl pyrrolidone (average molecular weight, 40,000) was used as a catalyst.

Two hours after the start of the reaction, the HFP conversion was 76%, and the HFPO selectivity was 82%.

EXAMPLE 45

The procedure of Example 1 was repeated wherein 1.2 g (8 milimoles) of hexafluoropropylene was used, and 20 ml of an aqueous sodium hypochlorite solution B-O (containing 40 milimoles of sodium hypochlorite and 0.5 milimole of sodium hydroxide) was used in place of the aqueous sodium hypochlorite solution A. The molar ratio of sodium hydroxide to hexafluoropropylene was 0.06/1, and the molar ratio of sodium hypochlorite to hexafluoropropylene was 5.0/1.

One hour after the start of the reaction, the HFP conversion was 87%, and the HFPO selectivity was 57%. In this case, even though the reaction was further continued, no increase in the HFP conversion was observed.

EXAMPLE 46

The procedure of Example 45 was repeated wherein 20 ml of an aqueous sodium hypochlorite solution B-1 (containing 40 milimoles of sodium hypochlorite and 2 milimoles of sodium hydroxide) was used. The molar ratio of sodium hydroxide to hexafluoropropylene was 0.25/1, and the molar ratio of sodium hypochlorite to hexafluoropropylene was 5.0/1.

One hour after the start of the reaction, the HFP conversion was 91%, and the HFPO selectivity was 72%.

EXAMPLE 47

The procedure of Example 45 was repeated wherein 20 ml of an aqueous sodium hypochlorite solution B-2 (containing 40 milimoles of sodium hypochlorite and 31 milimoles of sodium hydroxide) was used. The molar ratio of sodium hydroxide to hexafluoropropylene was 3.8/1, and the molar ratio of sodium hypochlorite to hexafluoropropylene was 5.0/1.

One hour after the start of the reaction, the HFP conversion was 99%, and the HFPO selectivity was 77%.

EXAMPLE 48

The procedure of Example 1 was repeated wherein 20 ml of an aqueous sodium hypochlorite solution C (containing 34 milimoles of sodium hypochlorite and 19 milimoles of sodium hydroxide) was used. The molar ratio of sodium hydroxide to hexafluoropropylene was 1.9/1, and the molar ratio of sodium hypochlorite to hexafluoropropylene was 3.4/1.

Fifteen minutes after the start of the reaction, the HFP conversion was 95%, and the HFPO selectivity was 78%. Thirty minutes after the start of the reaction, the HFP conversion was 99%, and the HFPO selectivity was 76%.

EXAMPLE 49

A 300-ml autoclave of glass was charged with 150 ml of an aqueous sodium hypochlorite solution B-3 (containing 300 milimoles of sodium hypochlorite and 60 milimoles of sodium hydroxide), 100 ml of F-113, 11 g (73 milimoles) of hexafluoropropylene, and 0.65 g (1.6 milimoles) of TOMAC. The reaction was carried out at a temperature of from $-10°$ C. to $-5°$ C. and a rate of stirring of 1,000 r.p.m. for a period of 25 minutes. The molar ratio of sodium hydroxide to hexafluoropropylene was 0.82/1, and the molar ratio of sodium hypochlorite to hexafluoropropylene was 4.1/1.

Gas chromatographic analysis of the products indicated that the HFP conversion was 96%, and the HFPO selectivity was 76%.

EXAMPLE 50

The procedure of Example 49 was repeated wherein 100 ml of diisopropyl ether was used in place of F-113 as an organic solvent, and the reaction was carried out for a period of 20 minutes.

The HFP conversion was 96%, and the HFPO selectivity was 70%.

EXAMPLE 51

The procedure of Example 49 was repeated wherein 100 ml of a mixed solvent of benzene and n-hexane (volume ratio, 1/9) was used in place of F-113 as an organic solvent, TOMAC was used in the amount of 0.33 g (0.8 milimole) in place of 0.65 g, and the reaction was carried out for a period of 30 minutes.

The HFP conversion was 80%, and the HFPO selectivity was 78%.

EXAMPLE 52

The procedure of Example 45 was repeated wherein 5.7 ml of an aqueous sodium hypochlorite solution C (containing 9.6 milimoles of sodium hypochlorite and 5.4 milimoles of sodium hydroxide) was used. The molar ratio of sodium hydroxide to hexafluoropropylene was 0.68/1, and the molar ratio of sodium hypochlorite to hexafluoropropylene was 1.2/1.

Fifteen minutes after the start of the reaction, the HFP conversion was 50%, and the HFPO selectivity was 73%.

EXAMPLE 53

The procedure of Example 45 was repeated wherein 15.2 ml of an aqueous sodium hypochlorite solution D (containing 9.6 milimoles of sodium hypochlorite and 6.1 milimoles of sodium hydroxide) was used. The molar ratio of sodium hydroxide to hexafluoropropylene was 0.76/1, and the molar ratio of sodium hypochlorite to hexafluoropropylene was 1.2/1.

Fifteen minutes after the start of the reaction, the HFP conversion was 77%, and the HFPO selectivity was 74%.

EXAMPLE 54

The procedure of Example 1 was repeated wherein 20 ml of an aqueous sodium hypochlorite solution B-4 (containing 20 milimoles of sodium hypochlorite and 8 milimoles of sodium hydroxide) was used. The molar ratio of sodium hydroxide to hexafluoropropylene was 0.80/1, and the molar ratio of sodium hypochlorite to hexafluoropropylene was 2.0/1.

One hour after the start of the reaction, the HFP conversion was 91%, and the HFPO selectivity was 80%.

EXAMPLE 55

In this example, hexafluoropropylene oxide was prepared from hexafluoropropylene by the use of continuous reaction equipment as illustrated in the FIGURE, comprising a stationary mixer 1 (length: 150 mm: including a twisted blade type mixing element), a 160-ml tubular reactor 2, a decanter 3, a HFPO distillation column 4, and a 1,000-ml organic phase tank 5.

The stationary mixer 1, tubular reactor 2, and decanter 3 were cooled down to $-10°$ C., and the pressure was maintained at 3 kg/cm$^2$ (gauge pressure) with nitrogen gas. A F-113 solution containing 0.045 mole/l of TOMAC was circulated in the reaction equipment at a flow rate of 33 ml/min. Then, an aqueous sodium hypochlorite solution B-4 (containing 1.0 mole/l of sodium hypochlorite and 0.40 mole/l of sodium hydroxide) was introduced into the stationary mixer 1 at a flow rate of 27 ml/min, and was withdrawn simultaneously from the decanter 3. Hexafluoropropylene was introduced into an organic phase line before the stationary mixer 1 at a flow rate of 2.10 g/min (14.0 milimoles/min) to start the reaction. In the tubular reactor 2, the molar ratio of sodium hydroxide to hexafluoropropylene was 0.77/1, and the molar ratio of sodium hypochlorite to hexafluoropropylene was 1.9/1. The organic phase and aqueous phase were finely dispersed in the stationary mixer 1, and passed through the tubular reactor 2 in the dispersed state during which the reaction proceeded between the two phases. The reaction solution leaving the tubular reactor 2 was introduced into the decanter 3 where it was separated into the organic phase and aqueous phase. The aqueous phase was discharge out of the reaction equipment. The organic phase containing the formed hexafluoropropylene oxide was sent to the HFPO distillation column 4 were the formed hexafluoropropylene oxide and the unreacted hexafluoropropylene were separated from the organic phase. During the period from 1 to 2 hours after the start of the reaction, the average distillation rate of hexafluoropropylene oxide was 1.80 g/min (10.8 milimoles/min), and the average distillation rate of hexafluoropropylene was 0.02 g/min (0.13 milimoles/min). The organic phase from which the hexafluoropropylene oxide and hexafluoropropylene had been distilled away in the HFPO distillation column 4 was sent to the organic phase tank 5and, thereafter, was returned to the stationary mixer 1.

While the invention has been described in detail and with reference to specific embodiment thereof, it will be apparent to one skilled in the art that various changes and modifications can be made therein without departing from the spirit and scope thereof.

What is claimed is:

1. A process for producing hexafluoropropylene oxide from hexafluoropropylene using hypochlorite as an oxidizing agent, which comprises epoxidizing hexafluoropropylene in a two-phase system of an aqueous phase and an organic phase which is immiscible in the aqueous phase, said hypochlorite being dissolved or dispersed in the aqueous phase in the presence of an inorganic base at a temperature of between $-25°$ C. and $60°$ C., in the presence of a lipophilic quaternary ammonium salt, catalyst the total number of carbon atoms in quaternary ammonium ion being not less than 10 per quaternary ammonium ion, to produce HFPO.

2. A process as claimed in claim 1, wherein the reaction is carried out in the presence of at least 0.1 gram equivalent of the inorganic base per mole of the hexafluoropropylene.

3. A process as claimed in claim 1, wherein the inorganic base is sodium hydroxide.

4. A process as claimed in claim 1, wherein the hypochlorite is selected from the group consisting of sodium hypochlorite, calcium hypochlorite and potassium hypochlorite.

5. A process as claimed in claim 1, wherein the reaction is carried out at a temperature ranging between $-25°$ C. and $60°$ C.

6. A process as claimed in claim 1, wherein the organic phase contains at least one solvent selected from the group consisting of chlorinated hydrocarbons and fluorinecontaining solvents.

7. A process as claimed in claim 1, wherein after the synthesis of hexafluoropropylene oxide from hexafluoropropylene by the two-phase reaction, the organic phase and aqueous phase are separated from each other, the hexafluoropropylene oxide is isolated from the organic phase, and hexafluoropropylene is added to the residual organic phase containing the catalyst and the resulting mixture is re-used in the two-phase reaction.

8. A process as claimed in claim 1, wherein the available chlorine content in the aqueous phase is from 1% to 25%.

9. A process as claimed in claim 18, wherein the available chlorine content in the aqueous phase is from 3% to 20%.

10. A process as claimed in claim 1, wherein the catalyst is contained in an amount of from 0.0001 to 10 moles per gram equivalent of hypochlorite ion.

11. A process as claimed in claim 10, wherein the catalyst is contained in an amount of from 0.001 to 1 mole per gram equivalent of hypochlorite ion.

12. A process as claimed in claim 1, wherein the organic phase is from 0.05 to 20 times as much as the aqueous phase.

13. A process as claimed in claim 12, wherein the organic phase is from 0.2 to 5 times as much as the aqueous phase.

14. A process as claimed in claim 5, wherein the reaction is carried out at a temperature ranging between $-20°$ C. to $40°$ C.

* * * * *